US008324388B2

(12) United States Patent
Kotrel et al.

(10) Patent No.: US 8,324,388 B2
(45) Date of Patent: Dec. 4, 2012

(54) DEHYDROGENATION PROCESS

(75) Inventors: Stefan Kotrel, Speyer (DE); Martin Ernst, Heidelberg (DE)

(73) Assignee: BASF Aktiengesellschaft (DE)

( * ) Notice: Subject to any disclaimer, the term of this patent is extended or adjusted under 35 U.S.C. 154(b) by 1085 days.

(21) Appl. No.: 12/279,548

(22) PCT Filed: Feb. 7, 2007

(86) PCT No.: PCT/EP2007/051149
§ 371 (c)(1),
(2), (4) Date: Aug. 15, 2008

(87) PCT Pub. No.: WO2007/093533
PCT Pub. Date: Aug. 23, 2007

(65) Prior Publication Data
US 2009/0099368 A1     Apr. 16, 2009

(30) Foreign Application Priority Data

Feb. 15, 2006  (EP) .................................. 06101723

(51) Int. Cl.
*C07D 213/133*    (2006.01)
(52) U.S. Cl. ...................................... 546/252
(58) Field of Classification Search .............. None
See application file for complete search history.

(56) References Cited

U.S. PATENT DOCUMENTS

| 3,399,246 | A | | 8/1968 | Traynor at al. |
| 3,670,044 | A | | 6/1972 | Drehman et al. |
| 4,401,819 | A | * | 8/1983 | Cordier et al. ............. 546/252 |
| 4,762,929 | A | | 8/1988 | Rebafka |
| 5,733,518 | A | | 3/1998 | Durante et al. |
| 6,538,139 | B1 | | 3/2003 | Schäfer et al. |
| 7,161,039 | B2 | * | 1/2007 | Steinbrenner et al. ........ 564/485 |

FOREIGN PATENT DOCUMENTS

| CA | 2558547 | 10/2005 |
| EP | 0155649 A2 | 9/1985 |
| EP | 0323115 A1 | 7/1989 |
| EP | 1291081 A1 | 3/2003 |
| WO | WO-94/29021 A1 | 12/1994 |
| WO | WO-2005/097715 A1 | 10/2005 |

* cited by examiner

*Primary Examiner* — Joseph K. McKane
*Assistant Examiner* — Alicia L Otton
(74) *Attorney, Agent, or Firm* — Connolly Bove Lodge & Hutz LLP

(57) ABSTRACT

Processes comprising: providing a dehydrogenatable compound; and subjecting the dehydrogenatable compound to a dehydrogenation reaction at a temperature of from 150 to 400° C., in the presence of oxygen, and at a temperature profile of the dehydrogenation reaction which does not differ substantially from the temperature profile of the dehydrogenation reaction in the absence of oxygen under otherwise identical conditions.

10 Claims, 1 Drawing Sheet

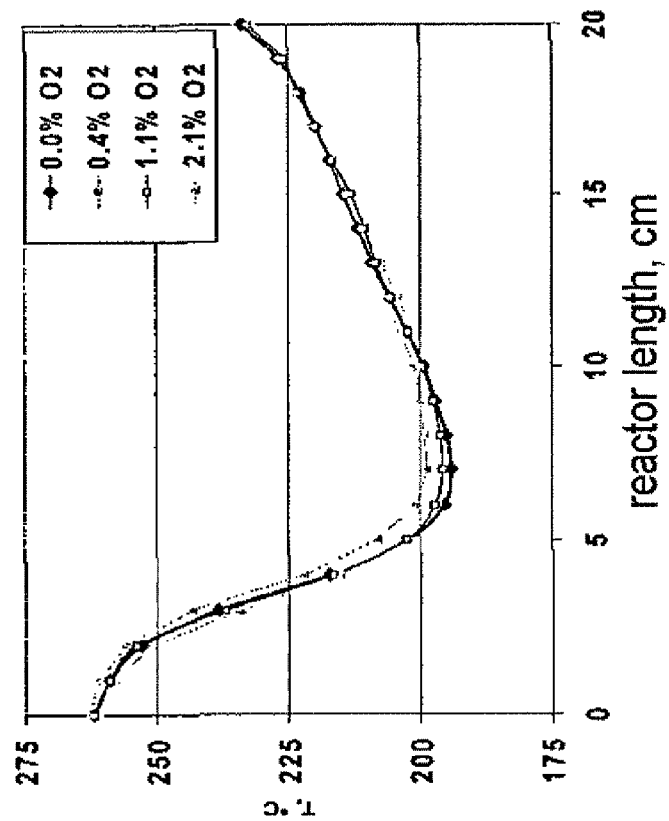
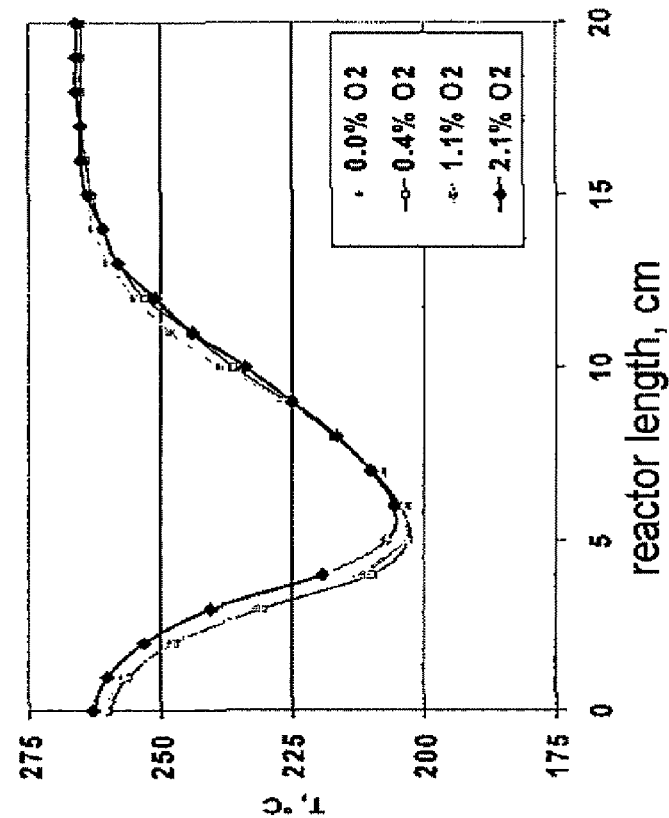

DEHYDROGENATION PROCESS

CROSS-REFERENCE TO RELATED APPLICATIONS

This application is a national stage application, under 35 U.S.C. §371, of PCT/EP2007/051149, filed Feb. 7, 2007, which claims priority of European Patent Application No. 06101723.2, filed Feb. 15, 2006.

BACKGROUND OF THE INVENTION

It is known that organic compounds can be catalytically dehydrogenated and converted into corresponding unsaturated or aromatic compounds.

Usually, heterogeneous catalysts are used here. In the case of heterogeneous catalysts, a distinction is made between pure metals (for example in the form of colloidal metals, metal sponges or metal blacks, metal powders or wires), metal compounds (e.g. metal oxides, sulfides or nitrides; metal glasses) and supported catalysts. Dehydrogenation catalysts usually used are supported catalysts. Supported catalysts substantially comprise catalyst support (support) and active component.

It is known that catalysts lose activity during the reaction. This takes place, for example, due to deposition and degradation of compounds on the catalyst surface. This phenomenon referred to as coking by the person skilled in the art leads to blocking of reactive centers and hence to deactivation of the catalyst.

It is advantageous to design the reaction procedure so that the deactivation of the catalyst is reduced in the reaction itself.

This can be effected by intrinsic improvement of the catalyst system. This approach is followed, for example, in EP-A 0 155 649. There, the conversion of piperidine derivatives into pyridines is carried out over a Pd/Al$_2$O$_3$ catalyst which additionally comprises from 0.1 to 10% by weight of MgCl$_2$. This process is distinguished by an improvement in the achievable catalyst lives.

Furthermore, the deactivation of the catalyst can be suppressed by improving the course of the reaction during the hydrogenation.

EP-A 1 291 081 describes a process for the preparation of pyrroles and pyridines from pyrrolidones and piperidines, respectively, in the presence of a supported noble metal catalyst, in which the course of the synthesis is influenced without changing the chemical composition of the catalyst. EP-A 1 291 081 teaches that the formulation of valeronitrile over a ZrO$_2$-supported Pd/Pt catalyst can be suppressed by the addition of water to the reactant stream. The addition of water requires an additional outlay in terms of process engineering and energy.

In the oxidative dehydrogenation, the dehydrogenation reaction takes place in the presence of oxygen. The heat input required for the dehydrogenation is effected by the combustion of hydrogen directly during the dehydrogenation reaction instead of via external heat input. The dehydrogenation and the oxidation can take place over the same catalyst or different catalysts. The dehydrogenation and the oxidation can take place together in the same location or separately.

EP-A 0 323 115 discloses the dehydrogenation of C$_2$-C$_{30}$-paraffins in the presence of steam and in the presence of a single catalyst. This preferably comprises platinum, potassium and tin on alumina as a catalyst support. The oxygen is used in about 0.01 to two molar amounts, based on the paraffin. The dehydrogenation is carried out at a temperature of from 400 to 900° C.

U.S. Pat. No. 3,670,044 describes the dehydrogenation of alkanes, alkylalkanes and arylalkanes having 2 to 12 carbon atoms in the presence of a catalyst which preferably comprises platinum and optionally tin on a zinc aluminum spinel as a catalyst support. The oxygen is used in from 0.02 to 0.15 molar amounts, based on the hydrocarbon used. The dehydrogenation is carried out at a temperature of from 510 to 621° C.

U.S. Pat. No. 5,733,518 describes the dehydrogenation of C$_3$-C$_{10}$-alkanes in the presence of nickel catalysts. Dehydrogenation and oxidation take place over different catalysts at different points in the reactor. The dehydrogenation is effected over a catalyst consisting of sulfided nickel on a non acidic support, such as neutralized alumina and zeolite. The hydrogen oxidation is effected in the presence of a phosphate of the metals germanium, tin, lead, arsenic, antimony and bismuth as a catalyst with 5.05 mol % oxygen in the feed at a temperature of from 300 to 600° C.

WO-A 94/29021 describes catalysts whose catalyst supports substantially comprise a mixed oxide of magnesium and aluminum, and which furthermore comprise a noble metal of group VIII and further components. These catalyze the dehydrogenation of C$_2$-C$_{30}$-hydrocarbons with or without simultaneous oxidation of hydrogen at a temperature of from 400 to 700° C.

BRIEF SUMMARY OF THE INVENTION

The present invention relates to a process for the dehydrogenation of dehydrogenatable compounds at a temperature of from 150 to 400° C. in the presence of oxygen.

Further embodiments of the present invention are described in the claims, the description and the examples. Of course, the abovementioned features of the subject matter according to the invention and the features of the subject matter according to the invention which are still to be explained below can be used not only in the respective stated combination but also in other combinations without departing from the scope of the invention.

The object of the present invention was to provide a process for the dehydrogenation of dehydrogenatable compounds, in which the activity and selectivity are improved. In addition, it was the object to provide a process for the dehydrogenation of heterocyclic compounds which increases the life without losses of yield occurring.

The object is achieved by providing a process for the dehydrogenation of dehydrogenatable compounds, in which the dehydrogenation reaction takes place in the presence of oxygen, with the proviso that the temperature profile of the dehydrogenation reaction in the presence of oxygen does not substantially differ from the temperature profile of the dehydrogenation reaction in the absence of oxygen and otherwise identical conditions.

The addition of oxygen is also referred to as airbleed in the context of this invention.

The starting material is passed over a suitable catalyst at a suitable temperature, which does not exceed 400° C., and a suitable pressure.

In the context of this invention, a compound can be dehydrogenated if it is in principle capable of eliminating at least one molecule of hydrogen per molecule of the compound used. It is also possible that two or more molecules of hydrogen can be eliminated from one molecule of the compound used. The amount of hydrogen liberated can be collected and determined. If the dehydrogenation is carried out with addition of hydrogen, this added amount must be taken into account in the determination.

Alternatively, the relative number of multiple bonds formed can be determined. This is effected, for example, by infrared (IR) spectroscopy, near infrared (NIR) spectroscopy and nuclear magnetic resonance (NMR) spectroscopy.

BRIEF DESCRIPTION OF THE SEVERAL VIEWS OF THE DRAWING

The foregoing summary, as well as the following detailed description of the invention, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

In the drawings:

FIG. 1 is a graphical representation of the temperature profiles of two processes according to two embodiments of the present invention.

DETAILED DESCRIPTION OF THE INVENTION

Suitable starting materials for the dehydrogenation reaction are, for example, monocyclic dehydrogenatable hydrocarbons having 3 to 10 ring atoms, one or more H atoms being capable of being substituted by identical or different radicals. Preferred compounds are cyclohexane and cyclohexene, it being possible substitute one or more H atoms by identical or different radicals. A preferred target compound is styrene.

Suitable starting materials for the dehydrogenation reaction are also polycyclic hydrocarbons having 3 to 10 ring atoms per ring, the rings being present in isolated, fused and/or spiroid form and it being possible for one or more H atoms to be substituted by identical or different radicals and for at least one of the rings to be capable of undergoing dehydrogenation. Examples of such compounds are phenylcyclohexane, cyclohexylbiphenyl, decal in and tetralin.

Suitable starting materials for the dehydrogenation reaction are also monocyclic or polycyclic hydrocarbons having one or more heteroatoms in the ring, the ring being present in isolated, fused and/or spiroid form and it being possible for one or more H atoms to be substituted by identical or different radicals and for at least one of the rings to be capable of undergoing dehydrogenation. Examples of such compounds are pyrrolidine, pyrrolidone, tetrahydrofuran, piperidine and octahydroindole.

Preferred target compounds are pyrimidine, pyridazine, pyrroles, indole, quinoline, imidazole or furan from the completely or partly saturated homologous heterocyclic compounds, it being possible for one or more H atoms to be substituted by identical or different radicals.

In all the abovementioned compounds, the number of identical or different radicals is such that at least one ring can be dehydrogenated; preferably, the number of identical or different radicals is from 0 to 3.

The abovementioned radicals may be unsubstituted hydrocarbon radicals, such as alkyl (preferably $C_1$-$C_4$-alkyl—i.e. methyl, ethyl, n-propyl, isopropyl, n-butyl, isobutyl, sec-butyl, tert-butyl), alkenyl (preferably $C_2$-$C_4$—for example vinyl, allyl) and alkynyl (preferably $C_2$-$C_4$—for example propargyl).

Furthermore, possible radicals are —OH, —OR, —OC(O)R, —$NH_2$, —NHR, —NRR', —CN, —C(O)OH, —C(O)OR, —C(O)$NH_2$, —C(O)NHR, —C(O)$NR_2$, —CHO, —C(O)R, where R and R', independently of one another, are alkyl, alkenyl and/or alkynyl as defined above. Furthermore, the radicals are selected from the group consisting of alkyl, alkenyl and alkynyl as defined above, one or more H atoms being substituted by identical or different substituents, such as —OH, —OR, —OC(O)R, —$NH_2$, —NHR, —NRR', —CN, —C(O)OH, —C(O)OR, —C(O)$NH_2$, —C(O)NHR, —C(O)$NR_2$, —CHO, —C(O)R, where R and R', independently of one another, are alkyl, alkenyl and/or alkynyl as defined above.

These are, for example, —$CH_2OH$, —$CH_2CN$ and —$CH_2CH(OH)CH_3$.

According to the invention, isolated means that the rings are linked to one another via a bond via at least one bridge atom.

According to the invention, fused means that two rings are bonded to one another via their edges.

According to the invention, spiroid means that two rings have exactly one common ring atom.

Preferred compounds are decalin, hydroazulene and tetralin, it being possible for one or more H atoms to be substituted by identical or different radicals.

The cyclic hydrocarbon rings are dehydrogenated by using the catalysts according to the invention. At least one of the dehydrogenatable hydrocarbon rings, which, if appropriate, may comprise heteroatoms is partly dehydrogenated or dehydrogenated to the maximum extent. The dehydrogenated ring is preferably aromatic after the reaction.

In the case of rings monosubstituted or polysubstituted by organic radicals, dehydrogenation of the organic radicals may take place. In comparison with the dehydrogenation of one or more rings, the dehydrogenation of the organic radicals may take place faster, more slowly or at the same rate.

In the context of the present application, the term starting material means a pure compound or a mixture of compounds. Pure compounds are preferably used.

The starting material is preferably gaseous. Either it is already gaseous at room temperature or it is preheated under suitable conditions in order to be present in gaseous form. Such preheating can be effected, for example, with the aid of an evaporator. The heat input can, if appropriate, be effected via a carrier material.

Furthermore, the starting material may be fed to a gas. The gas may be saturated or supersaturated by the starting material.

The process according to the invention is carried out at temperatures of from 150 to 400° C., preferably from 170 to 300° C., particularly preferably from 200 to 270° C.

The dehydrogenation is carried out at suitable temperatures. The choice of the temperature is dependent, for example, on the type and the concentration of the starting materials and on the catalyst used.

If appropriate, a ramp procedure may be desired.

The dehydrogenation is carried out at suitable pressures. The process according to the invention can be carried out at pressures of from 0.01 to 50 bar, preferably from 0.1 to 5 bar, particularly preferably at atmospheric pressure.

The pressure data are to be understood as being absolute pressures.

The dehydrogenation catalysts used are usually supported catalysts. In the context of this description, a supported catalyst is designated as a catalyst in which the active component is present on a catalyst support.

In principle, any dehydrogenation catalyst is suitable, supported catalysts being preferred.

In principle, any supported catalyst is suitable.

A preferred catalyst support is zirconium oxide. This may be present in various modifications. Zirconium oxide is found as naturally occurring baddeleyite. Synthetic zirconium oxide is usually obtainable by calcination of other zirconium compounds. As modifications known at atmospheric pressure, a distinction is made between cubic, tetragonal (metastable) and monoclinic (stable). The cubic modification can be stabilized at room temperature by addition of any suitable additives, such as magnesium oxide, calcium oxide, yttrium oxide or oxides of the metals of the 3rd group of the Periodic Table of the Elements. For this purpose, these are typically added in amounts of from 3% by weight to 8% by weight, based on the total mass of the catalyst support before any heating steps.

Furthermore, partially stabilized zirconium oxides (PSZ) are known and are obtainable by precipitation of metastable tetragonal zirconium oxide in particles of cubic zirconium oxide.

In addition, tetragonal zirconium oxide polycrystals are known (TZP). A high-pressure modification is the orthorhombic one, which can be stabilized at atmospheric pressure by adding 12 mol % of more of niobium oxide, tantalum oxide or mixtures thereof. In addition, further substoichiometric compounds of zirconium and oxygen or solutions of oxygen in zirconium, $ZrO_n$, where n<2, are also known.

A preferred modification of zirconium oxide as a constituent of the catalyst support is the monoclinic modification.

Zirconium oxide usually comprises hafnium, silicon, sulfur and sodium. Even in purified form, these elements are present in the catalyst support. The proportion of hafnium oxide is preferably 2% by weight or less. The proportion of sulfur is preferably 100 mg/kg or less.

A particularly preferred catalyst support comprises at least 97% of zirconium oxide.

In a further embodiment, other oxidic and nonoxidic support substances are suitable as catalyst supports. These support substances may have little catalytic activity or may be inert substances. However, they may also be substances which interact with the catalytically active component and hence have a more or less pronounced effect on its catalytic properties. These support substances are preferably solids which are heat-stable up to the sintering temperature of the catalytically active material. Distinguishing criteria of these support substances are, for example, their chemical characteristics and specific surface area.

Suitable support substances are natural oxides, such as natural clays, silicates, aluminosilicates, kieselguhr, diatomite, spinels, pumice, titanates; synthetic metal oxides, such as aluminas, magnesium oxides, silicas, ground glass, silica gels, silicon aluminum oxides, spinels, zinc oxides, titanium oxides; metal carbides, such as silicon carbides; active carbon of animal or vegetable origin; soot, graphite, carbon black; nitrides; and compacts prepared by a powder metallurgical method by means of sintering and consisting of metal powder particles (if appropriate, with the use of metal compounds and non metals).

These may occur in various physical modifications. Examples for modifications of alumina are $\gamma$-$Al_2O_3$, $\eta$-$Al_2O_3$ and $\alpha$-$Al_2O_3$.

If appropriate, the catalyst support comprises further additives. These include in particular pore formers or binders or mixtures thereof. Pore formers serve the purpose of producing a larger internal surface area. Suitable pore formers are ammonium nitrate, citrates, polyalkylene oxides, such as polyethylene oxide, carbohydrates, such as cellulose, starch or sugar, natural fibers, pulp or synthetic polymers, such as polyvinyl alcohol or mixtures thereof.

Binders serve the purpose of combining smaller particles to give larger agglomerates and thus ensure greater mechanical strength.

Aluminum and/or silicon precursors, for example in the form of hydroxides, preferably in colloidal form, can be used as binders. These are converted into alumina and/or silica by heating.

The catalyst support may furthermore comprise further additives. Further additives are, for example, known compounds which influence the rheology.

The active component may be a substance of groups 7 to 11 of the Periodic Table of the Elements. The Periodic Table of the Elements according to IUPAC on Oct. 3, 2005 is applicable. In particular, the elements Mn, Re, Fe, Ru, Os, Co, Rh, Ir, Ni, Pd, Pt, Cu, Ag and Au are meant thereby. In a particularly preferred embodiment, the catalytically active material is platinum, palladium or mixtures thereof.

Mixtures are both macroscopic mixtures of platinum and palladium particles and microscopic mixtures, such as, for example, sintered materials or alloys.

Methods for applying the catalytically active material to the catalyst support are known per se.

One form provided is the so-called coated catalyst, in which the catalyst support is impregnated with the solution of a precursor of the catalytically active material, for example of a noble metal salt.

In one embodiment, the catalyst support is impregnated with solutions or suspensions of one or more noble metal compounds, which are converted into active components after appropriate treatment.

The impregnation can be effected continuously or batchwise. The impregnation can be effected once or several times. The impregnation can be effected by the following methods known to the person skilled in the art: from supernatant solution, by spraying, by evaporation of the solution or by melting of compounds. Impregnation is preferably effected from supernatant solution.

It is preferable to use the catalytically active material in the form of a noble metal salt. In a preferred embodiment noble metal salts whose anions can easily be removed by thermal treatment are used.

In a particularly preferred embodiment, noble metal salts having anions selected from the group consisting of the nitrates and acetates are used.

A preferred noble metal compound is palladium nitrate.

The catalytically active material can in general be present in the catalyst in the active form on the catalyst support. This active form is dependent on the catalytically active material chosen in each case.

In an embodiment of the present invention, the catalytically active material is present in inactive or slightly active form on the support. In a further embodiment, the catalytically active material is present in active form on the support. The catalytically active material is in general active in the reduced form. The catalytically active material must consequently generally be reduced in the case of covalently or electrostatically bonded forms of the catalytically active material. The reduction can be effected, for example, by heat treatment under pure hydrogen.

The catalytically active material is present in general in amounts such that catalytic activity is ensured. Depending on the respective catalytically active material, this is the case, for example with Pd, as a rule at a content of 0.1% by weight or more, preferably at 0.3% by weight and particularly preferably at 0.5% or more of the catalytically active material, based on the catalyst.

The proportion of the catalytically active material may be, for example, up to 50% by weight, preferably up to 10% by weight. The proportion may also be greater; in general, it is lower, for example up to 5% by weight, in particular up to 1% by weight, based on the catalyst.

The catalyst size and shape (geometry) influence the dehydrogenation reaction.

Thus, more finely distributed catalysts having a large surface area often permit a better conversion but have a higher flow resistance. A higher flow resistance is also achieved by dense packing. Coarser catalysts frequently permit faster flow-through, but this often takes place at the expense of the conversion.

The catalyst is usually provided as bulk material in particle sizes of from 1.5 to 6 mm. Depending on the temperature and pressure range of the desired reaction, a certain macroscopic form may also be advantageous. Depending on the reactor type, the catalyst is provided, for example, in the form of pills, extrudates, hollow extrudates, wagon wheels, stars, spheres of various diameter or powders. The person skilled in the art will select an appropriate catalyst size and shape taking into account the reaction conditions, for example temperature and pressure range, and reactor size.

The catalyst can, if required, be regenerated after the dehydrogenation reaction under conditions known to the person skilled in the art.

For example, a catalyst can be thermally treated. The regeneration temperature is preferably chosen so that sintering of the catalytically active component is avoided.

If desired, the regeneration can be carried out in the presence of substances which promote the regeneration. Oxygen is preferred and is metered in, for example, in the form of air.

In the process according to the invention, the dehydrogenation takes place in the presence of oxygen. Oxygen is fed to the reaction preferably in the form of air. The use of pure oxygen or other oxygen-containing gas mixtures is also possible for carrying out the process according to the invention.

In the context of the present invention, an influence on the reaction temperature is regarded as being not substantial when the temperature in the presence of oxygen and the temperature in the absence of oxygen differ by only a few percent, for example by 3% or less, preferably by 2% or less, particularly preferably by 1% or less, on the absolute temperature scale. The percentage deviation is the difference between the two temperatures divided by the higher temperature value.

For the temperature measurement, the temperature may be measured at one or more arbitrary points in the reactor. In this context, the person skilled in the art uses the term temperature profile of the reaction. In order to determine the influence of the oxygen on the reaction, however, only temperature values which were measured at comparable times at the same point may be compared with one another. Furthermore, the measurement must be effected with the same temperature element or with a calibrated temperature element.

The oxygen is used in amounts in which the addition has substantially no observable influence on the temperature profile.

Preferably, the oxygen is mixed with the feed stream.

In the context of the present application, the term "feed stream" designates any stream which comprises the starting material and leads in the direction of the reactor. One or more feed streams may be present.

Oxygen may be added in amounts of 0.05% by volume and 10% by volume, based on the total streams fed to the reactor, with the proviso that the temperature profile of the dehydrogenation reaction in the presence of oxygen doesn't differ substantially, i.e. differs only slightly, from the temperature profile of the dehydrogenation reaction in the absence of oxygen under otherwise identical conditions.

In a preferred embodiment, the dehydrogenation reaction is carried out so that the oxygen is completely consumed in the dehydrogenation. Preferably, the oxygen is not consumed for the conversion to carbon dioxide $CO_2$.

Furthermore, the reaction can be carried out in the presence of suitable further additives. Preferred further additives are suitably inert substances which serve as a carrier medium, for example solvents or carrier gases. These frequently have the object of diluting the reactant stream and/or removing heat of reaction. A preferred carrier medium is nitrogen.

Furthermore, process-improving substances are suitable as further additives. A preferred process-improving substance is hydrogen.

All substances can be metered into the reactor separately from one another or together. Furthermore, different substances may be premixed and metered separately from the others into the reactor.

A mixture is preferably a gaseous mixture.

Preferably, all substances are combined before the reactor.

Particularly preferably, an oxygen-containing stream and an $H_2$- and $N_2$-containing stream are mixed and this new mixture is then mixed with an organic feed.

In a further particularly preferred embodiment, an $H_2$- and $N_2$-containing stream and an organic feed are mixed and this new mixture is then mixed with the oxygen-containing stream.

The flow rate of any stream entering the reactor may be 0.5 cm/s or higher. The flow rate of any stream entering the reactor is not greater than 100 cm/s. Preferably, the flow rate of any stream entering the reactor is from 1 cm/s to 30 cm/s. In a particularly preferred embodiment, the flow rate of any stream entering the reactor is from 2 cm/s to 10 cm/s.

In the case of at least two streams entering the reactor, the flow rates of these streams may be identical or different.

Where only one stream enters the reactor and only one stream leaves the reactor, the flow rate of the stream leaving the reactor is usually higher than the flow rate of the stream entering the reactor owing to the hydrogen liberated. For example, the flow rate of the stream leaving the reactor may be twice as high.

The oxygen concentration of all streams entering the reactor is on average from 0.05 to 10% by volume, preferably from 0.1 to 5% by volume, particularly preferably from 0.3 to 3% by volume, of $O_2$.

The dehydrogenation reaction is carried out in a suitable reactor. One embodiment is the dehydrogenation reaction in a fixed-bed reactor. This is preferably operated adiabatically.

A further embodiment is the provision of a catalyst bed in a plurality of parts, so-called trays, with intermediate heat exchangers. The design as a tube-bundle reactor is also possible.

Furthermore, the dehydrogenation reaction may be carried out in suspension and over gas-solid fluidized beds.

The invention is explained in more detail below with reference to examples. These examples are descriptions and must on no account be regarded as limitations of the scope and of the underlying principles of the invention. Many modifications of the examples described can be derived from the examples and the description by the person skilled in the art. These modifications are likewise within the scope of the attached claims.

EXAMPLE

A 0.9% $Pd/ZrO_2$ catalyst which was prepared by impregnating 3 mm $ZrO_2$ extrudates with a $Pd(NO_3)_2$ solution was investigated for its activity with respect to the 3-methylpiperidine (3-MPIP) dehydrogenation to 3-picoline (3-PIC) in a tubular reactor having an internal diameter of 26 mm. For this purpose 50 ml of the catalyst material was initially taken and was activated for 4 h at 80° C. in a 20% by volume $H_2$ (in $N_2$) atmosphere and then at 200° C. under pure $H_2$ for 3 h. The 3-MPIP metering was then started. For the 3-MPIP metering, from 30 to 120 ml/h of the starting material were passed into an evaporator and completely vaporized into a carrier gas stream. The carrier gas consisted of 20% per volume of $H_2$, 0-10% by volume of air and 70-80% by volume of $N_2$. The total volume flow rate of the carrier gas corresponded to 20 l/h. The gaseous mixture of starting materials was passed over the catalyst bed after the evaporator. The dehydrogenation was carried out at 265° C. and atmospheric pressure. After a reaction time of 0.5 h three samples were taken at intervals of one hour and analyzed with regard to the 3-MPIP and the 3-PIC content. For the further course of the experiment, the 3-MPIP feed quantity was increased to twice the value after one hour in each case. After the space velocity had been increased twice, the initial space velocity (0.3 l per l per h) was finally run for one further hour and the PIC contents in the discharge were compared with the values of the first sample. The comparison of the PIC content of the first and of the last sample is a measure of the tendency of the catalyst to undergo deactivation.

TABLE 1

3-PIC contents, catalyst deactivation and C balance for four different oxygen concentrations

| Example No. | $O_2$ content | 3-PIC, % at 0.3 l/l · h | at 1.2 l/l · h | Deactivation | C balance |
|---|---|---|---|---|---|
| C1 *) | 0.0% | 99.4 | 78.0 | 0.27% | 98.6% |
| 1 | 0.4% | 99.5 | 78.7 | 0.17% | 98.6% |
| 2 | 1.1% | 99.4 | 80.7 | 0.13% | 98.3% |
| 3 | 2.1% | 99.5 | 81.9 | 0.03% | 98.4% |

*) Comparative example

Table 1 shows the measured 3-PIC contents of the product stream at a space velocity of 0.3 and 1.2 l of 3-MPIP per l of catalyst per h and the catalyst deactivation as a function of the $O_2$ partial pressure in the carrier gas stream. With increasing $O_2$ partial pressure, the catalyst deactivation decreases and the 3-PIC contents in the product at a space velocity of 1.2 l per l per h increase. For an oxygen content of 0.4%, the waste gas discharged from the reactor was investigated with regard to its $CO_2$ and CO content. $CO_2$ was virtually undetectable (3 ppm), and the CO concentration was below the determinable limit in concentration (<1 ppm).

FIG. 1 shows the temperature profiles of the dehydrogenation reactor for a space velocity of 0.3 and 1.2 l per l per h.

We claim:

1. A process comprising:
   providing 3-methylpiperidine; and
   subjecting 3-methylpiperidine to a dehydrogenation reaction at a temperature of from 150 to 400° C., in the presence of a feed stream comprising $O_2$, wherein the $O_2$ content of the feed stream after said feed stream has been metered in is from 0.05% by volume to 10% by volume.

2. The process according to claim 1, wherein subjecting the 3-methylpiperidine to a dehydrogenation reaction comprises mixing the feed stream comprising $O_2$ with a feed stream comprising the dehydrogenatable compound.

3. The process according to claim 2, wherein the reaction takes place in the presence of a catalyst.

4. The process according to claim 1, wherein the catalyst comprises a supported catalyst.

5. The process according to claim 1, wherein the catalyst comprises zirconium oxide as a catalyst support.

6. The process according to claim 1, wherein the reaction takes place in the presence of a catalytically active material.

7. The process according to claim 1, wherein the reaction takes place in the presence of a metal of the 10th Group of the Periodic Table.

8. The process according to claim 1, wherein 3-methylpicoline is formed by the dehydrogenation reaction.

9. The process according to claim 1, wherein the —$O_2$— is present in an amount of 0.1 to 5% by volume on average of all streams entering the reactor.

10. The process according to claim 1, wherein the —$O_2$— is present in an amount of 0.3 to 3% by volume on average of all streams entering the reactor.

* * * * *